(12) United States Patent
Ohta et al.

(10) Patent No.: US 6,423,843 B1
(45) Date of Patent: Jul. 23, 2002

(54) ENANTIOMERICALLY PURE SUBSTITUTED OXAAZA COMPOUNDS, SALTS OF THE SAME, AND PROCESSES FOR THE PREPARATION OF BOTH

(75) Inventors: Naoki Ohta; Toru Makino; Sadahiro Shimizu, all of Tokyo (JP)

(73) Assignee: Daiichi Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 09/719,687

(22) PCT Filed: Jun. 16, 1999

(86) PCT No.: PCT/JP99/03216

§ 371 (c)(1),
(2), (4) Date: Dec. 15, 2000

(87) PCT Pub. No.: WO99/65918

PCT Pub. Date: Dec. 23, 1999

(30) Foreign Application Priority Data

Jun. 17, 1998 (JP) .............................. 10-169387

(51) Int. Cl.[7] ..................... C07D 498/04; C07D 207/14
(52) U.S. Cl. ........................................ 544/91; 548/557
(58) Field of Search ............................. 544/91; 548/557

(56) References Cited

U.S. PATENT DOCUMENTS 5,532,364 A 7/1996 Schenke et al. ............ 544/105

FOREIGN PATENT DOCUMENTS

| DE | 43 09 964 A1 | 9/1994 |
|---|---|---|
| EP | 0 350 733 | 1/1990 |
| JP | 61-63652 | 4/1986 |
| JP | 2-69474 | 3/1990 |

OTHER PUBLICATIONS

Aurich, Hans Guenter et al., Preparation of Enantiomeric Pure 3–oxa–2, 7–diazabicyclo '3.3.0 Octanes and Their Conversation to other Bicyclic Ring Systems Z. Naturforsch, B: Chem. Sci. (1999) 54(1), pp 87–95 (XP–001007991) with English translation).

*Primary Examiner*—Richard L. Raymond
*Assistant Examiner*—Venkataraman Balasubramanian
(74) *Attorney, Agent, or Firm*—Sughrue Mion, PLLC

(57) ABSTRACT

This invention provides a method for conveniently obtaining a compound of formula (Ia) which is a production intermediate of antimicrobial compounds, in which a salt of optically active acid of formula (IIIa) is obtained by allowing a compound of formula (I), a ketone compound and an optically active acid to react with one another, converted into its free form and then hydrolyzed.

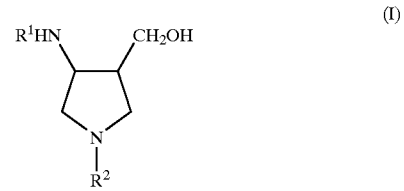

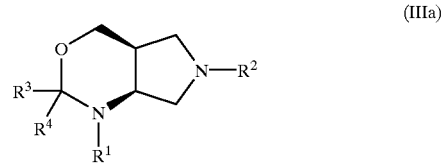

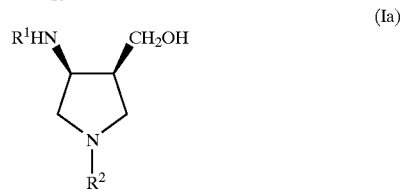

In the formula, $R^1$: hydrogen atom or alkyl, aryl or aralkyl group; $R^2$: hydrogen atom or alkyl, aryl, aralkyl, acyl, alkyloxycarbonyl, aralkyloxycarbonyl or substituted sulfonyl; these may further have substituents.)

19 Claims, No Drawings

ENANTIOMERICALLY PURE SUBSTITUTED OXAAZA COMPOUNDS, SALTS OF THE SAME, AND PROCESSES FOR THE PREPARATION OF BOTH

TECHNICAL FIELD

This invention relates to a production intermediate of antimicrobial compounds and a production method thereof.

BACKGROUND ART

3-Amino-4-fluoromethylpyrrolidinyl group is useful as substituent of quinolone compounds. This substituent exists in four stereoisomer forms originated from the configuration of amino group and fluoromethyl group on the pyrrolidine ring. That is, it exists in two isomers of cis and trans forms, and each of them exists in stereoisomer forms having enantiomorphic relationship, thus existing in four isomer forms. Most useful among these four isomers is (3S,4S)-3-amino-4-fluoromethylpyrrolidinyl group represented by the following formula:

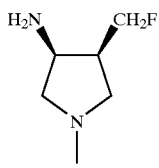

which has one of the enantiomorphic relationship of cis configuration and can provide a quinolone having excellent antimicrobial activity and safety.

In order to introduce this (3S,4S)-3-amino-4-fluoromethylpyrrolidinyl group into a quinolone compound, (3S,4S)-3-amino-4-fluoromethylpyrrolidine (formula (Va)):

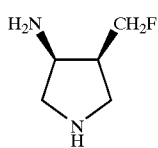

or a derivative thereof is required. In order to obtain this (3S,4S)-3-amino-4-fluoromethylpyrrolidine or a derivative thereof, it is convenient to obtain (3S,4S)-3-amino-4-hydroxymethylpyrrolidine (formula (IVa)):

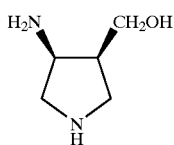

or a derivative thereof and introduce fluorine atom into the compound.

However, though cis-3-amino-4-hydroxymethylpyrrolidine as its racemic compound has been known, a method for the synthesis of (3S,4S)-3-amino-4-hydroxymethylpyrrolidine has not been known. Accordingly, the object of the invention of this application is to provide an efficient method for the production of (3S,4S)-3-amino-4-hydroxymethylpyrrolidine or a derivative thereof which is an excellent substituent supply source for efficiently obtaining excellent quinolone compounds.

DISCLOSURE OF THE INVENTION

As a result of extensive investigation, the present inventors have found that, when a racemic cis-3-amino-4-hydroxymethylpyrrolidine derivative represented by formula (I) is treated with mandelic acid as an optically active compound in acetone (or in the presence of an appropriate ketone compound), a condensed 1,3-oxazine derivative (III) is formed through the progress in an acetone- (or an appropriate ketone compound)-related ring closure reaction between the amino group and hydroxymethyl group, and one of the isomers of this compound forms a salt with the optically active mandelic acid and precipitates as crystals.

That is, it was revealed that separation of enantiomers of the compound of formula (I) is achieved by the precipitation of a salt of the oxazine compound represented by formula (III) with the optically active mandelic acid as crystals. In addition, it was revealed also that, when this salt is converted into its free form by removing mandelic acid and then hydrolyzed, a 3-amino-4-hydroxymethylpyrrolidine derivative comprised of one of the enantiomers is easily regenerated through ring opening of the oxazine ring.

Namely, the present invention was accomplished by finding that one of the enantiomers of the 3-amino-4-hydroxymethylpyrrolidine derivative can be obtained easily in this manner.

Accordingly, the present invention relates to a compound represented by the following formula (IIIa):

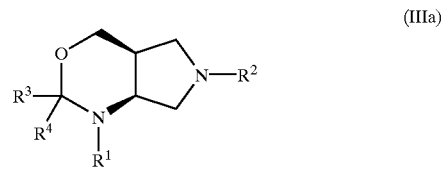

or formula (IIIb):

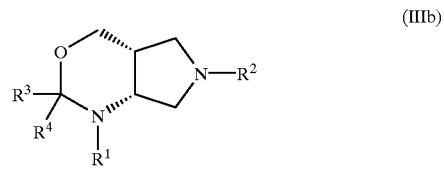

[in the above formulae, $R^1$ represents a hydrogen atom, an alkyl group having from 1 to 6 carbon atoms (which may have one or more substituents selected from the group consisting of a halogen atom and an alkoxyl group having from 1 to 6 carbon atoms), an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl groups having from 1 to 6 carbon atoms), an acyl group (which may be either aliphatic or aromatic; in the case of an aliphatic group, it has from 1 to 7 carbon atoms and may have one or more substituents selected from the group consisting of an aryl group, a halogen atom and an alkoxyl group having from 1 to 6 carbon atoms; and in the cases of an aryl group as an aromatic group and an aryl group as a substituent on the fatty chain in the case of an aliphatic group, it may have one or more substituents selected from the group consisting of a halogen atom, a nitro group, an alkyl group having from 1 to 6 carbon atoms and an alkoxyl group having from 1 to 6 carbon atoms), an alkyloxycarbonyl group having from 2 to 7 carbon atoms (the alkyl group moiety may have one or more substituents selected from the group consisting of a halogen atom and an alkoxyl groups having from 1 to 6 carbon atoms), or an aralkyloxycarbonyl group (wherein the aralkyl group has a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms);

$R^2$ represents a hydrogen atom, an alkyl group having from 1 to 6 carbon atoms (which may have one or more substituents selected from the group consisting of a halogen atom and an alkoxyl group having from 1 to 6 carbon atoms), an aralkyl group (having a structure in which an aryl group is substituted on an alkyl group having from 1 to 6 carbon atoms;

the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl groups having from 1 to 6 carbon atoms and an alkoxyl groups having from 1 to 6 carbon atoms), an acyl group (which may be either aliphatic or aromatic; in the case of an aliphatic group, it has from 1 to 7 carbon atoms and may have one or more substituents selected from the group consisting of an aryl group, a halogen atom and an alkoxyl group having from 1 to 6 carbon atoms; and in the cases of an aryl group as an aromatic group and an aryl group as a substituent on the fatty chain in the case of an aliphatic group, it may have one or more substituents selected from the group consisting of a halogen atom, a nitro group, an alkyl group having from 1 to 6 carbon atoms and an alkoxyl group having from 1 to 6 carbon atoms), an alkyloxycarbonyl group having from 2 to 7 carbon atoms (the alkyl group moiety may have one or more substituents selected from the group consisting of a halogen atom and an alkoxyl groups having from 1 to 6 carbon atoms), or an aralkyloxycarbonyl group (wherein the aralkyl group has a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms); and $R^3$ and $R^4$ each independently represents an alkyl group having from 1 to 6 carbon atoms (which may have one or more substituents selected from the group consisting of a halogen atom and an alkoxyl group having from 1 to 6 carbon atoms), or an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms); or $R^3$ and $R^4$ may together form a cyclic structure of from five-to eight-membered ring comprised of a polymethylene chain].

The present invention further relates to each of the following items.

A salt and a hydrate thereof, formed from a compound represented by a formula (IIIa) or formula (IIIb) and an acid as an optically active compound;

the aforementioned salt and a hydrate thereof, wherein the acid as an optically active compound is D-mandelic acid or L-mandelic acid;

the aforementioned salt and a hydrate thereof, wherein the acid as an optically active compound is D-mandelic acid;

the aforementioned salt and a hydrate thereof, wherein the acid as an optically active compound is L-mandelic acid;

the aforementioned salt and a hydrate thereof, wherein $R^3$ and $R^4$ are the same group;

the aforementioned salt and a hydrate thereof, wherein $R^3$ and $R^4$ are a methyl group;

the aforementioned salt and a hydrate thereof, wherein $R^1$ is a hydrogen atom;

the aforementioned salt and a hydrate thereof, wherein $R^2$ is selected from the group consisting of a tert-butoxycarbonyl group, a 2,2,2-trichloroethoxycarbonyl group, a benzyloxycarbonyl group, a p-methoxybenzyloxycarbonyl group, a p-nitrobenzyloxycarbonyl group, an acetyl group, a methoxyacetyl group, a trifluoroacetyl group, a chloroacetyl group, a pivaloyl group, a formyl group and a benzoyl group;

aforementioned salt and a hydrate thereof, wherein $R^2$ is a benzyloxycarbonyl group;

a method for producing a compound represented by a formula (Ia)

(Ia)

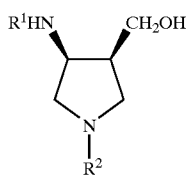

or formula (Ib):

(Ib)

[the above formulae,

R¹ represents a hydrogen atom, an alkyl group having from 1 to 6 carbon atoms (which may have one or more substituents selected from the group consisting of a halogen atom and an alkoxyl group having from 1 to 6 carbon atoms), an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl groups having from 1 to 6 carbon atoms), an acyl group (which may be either aliphatic or aromatic; in the case of an aliphatic group, it has from 1 to 7 carbon atoms and may have one or more substituents selected from the group consisting of an aryl group, a halogen atom and an alkoxyl group having from 1 to 6 carbon atoms; and in the cases of an aryl group as an aromatic group and an aryl group as a substituent on the fatty chain in the case of an aliphatic group, it may have one or more substituents selected from the group consisting of a halogen atom, a nitro group, an alkyl group having from 1 to 6 carbon atoms and an alkoxyl group having from 1 to 6 carbon atoms), an alkyloxycarbonyl group having from 2 to 7 carbon atoms (the alkyl group moiety may have one or more substituents selected from the group consisting of a halogen atom and an alkoxyl groups having from 1 to 6 carbon atoms), or an aralkyloxycarbonyl group (wherein the aralkyl group has a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms); and R² represents a hydrogen atom, an alkyl group having from 1 to 6 carbon atoms (which may have one or more substituents selected from the group consisting of a halogen atom and an alkoxyl group having from 1 to 6 carbon atoms), an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl groups having from 1 to 6 carbon atoms and an alkoxyl groups having from 1 to 6 carbon atoms), an acyl group (which may be either aliphatic or aromatic; in the case of an aliphatic group, it has from 1 to 7 carbon atoms and may have one or more substituents selected from the group consisting of an aryl group, a halogen atom and an alkoxyl group having from 1 to 6 carbon atoms; and in the cases of an aryl group as an aromatic group and an aryl group as a substituent on the fatty chain in the case of an aliphatic group, it may have one or more substituents selected from the group consisting of a halogen atom, a nitro group, an alkyl group having from 1 to 6 carbon atoms and an alkoxyl group having from 1 to 6 carbon atoms), an alkyloxycarbonyl group having from 2 to 7 carbon atoms (the alkyl group moiety may have one or more substituents selected from the group consisting of a halogen atom and an alkoxyl groups having from 1 to 6 carbon atoms), or an aralkyloxycarbonyl group (wherein the aralkyl group has a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms)], which comprises the following steps 1, 2 and 3, Step 1:

a step in which an enantiomer mixture of a compound represented by formula (I):

(I)

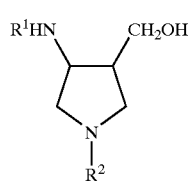

(in the formula, R¹ and R² are as defined in the foregoing, and the substituents R¹HN— and —CH₂OH on the pyrrolidine ring are in the cis configuration) is treated with a compound represented by formula (II):

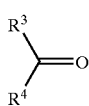
(II)

[in the formula,

R³ and R⁴ each independently represents an alkyl group having from 1 to 6 carbon atoms (which may have one or more substituents selected from the group consisting of a halogen atom and an alkoxyl group having from 1 to 6 carbon atoms), or an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms); or R³ and R⁴ may together form a cyclic structure of from five- to eight-membered ring comprised of a polymethylene chain] in the presence of an acid as an optically active compound, thereby obtaining a salt formed from either of a compound represented by formula (IIIa):

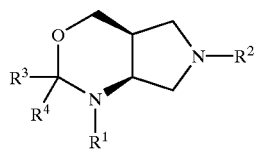
(IIIa)

or formula (IIIb):

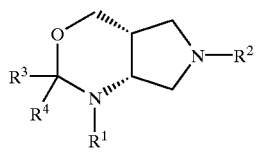
(IIIb)

and the optically active acid,

Step 2:

a step in which a free form is obtained by removing the acid from the salt formed from the compound represented by formula (IIIa) or (IIIb) and the optically active acid, and Step 3:

a step in which the compound represented by formula (Ia) or (Ib) is obtained by hydrolyzing the free form of the compound represented by formula (IIIa) or (IIIb);

the aforementioned production method, wherein the acid as an optically active compound is D-mandelic acid or L-mandelic acid;

a method for producing a compound represented by formula (Ia)

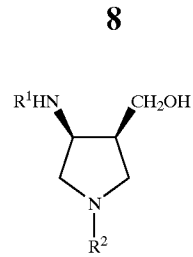
(Ia)

[in the above formula,

R¹ represents a hydrogen atom, an alkyl group having from 1 to 6 carbon atoms (which may have one or more substituents selected from the group consisting of a halogen atom and an alkoxyl group having from 1 to 6 carbon atoms), an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl groups having from 1 to 6 carbon atoms), an acyl group (which may be either aliphatic or aromatic; in the case of an aliphatic group, it has from 1 to 7 carbon atoms and may have one or more substituents selected from the group consisting of an aryl group, a halogen atom and an alkoxyl group having from 1 to 6 carbon atoms; and in the cases of an aryl group as an aromatic group and an aryl group as a substituent on the fatty chain in the case of an aliphatic group, it may have one or more substituents selected from the group consisting of a halogen atom, a nitro group, an alkyl group having from 1 to 6 carbon atoms and an alkoxyl group having from 1 to 6 carbon atoms), an alkyloxycarbonyl group having from 2 to 7 carbon atoms (the alkyl group moiety may have one or more substituents selected from the group consisting of a halogen atom and an alkoxyl groups having from 1 to 6 carbon atoms), or an aralkyloxycarbonyl group (wherein the aralkyl group has a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms); and R² represents a hydrogen atom, an alkyl group having from 1 to 6 carbon atoms (which may have one or more substituents selected from the group consisting of a halogen atom and an alkoxyl group having from 1 to 6 carbon atoms), an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl groups having from 1 to 6 carbon atoms and an alkoxyl groups having from 1 to 6 carbon atoms), an acyl group (which may be either aliphatic or aromatic; in the case of an aliphatic group, it has from 1 to 7 carbon atoms and may have one or more substituents selected from the group consisting of an aryl group, a halogen atom and an alkoxyl group having from 1 to 6 carbon atoms; and in the cases of an aryl group as an aromatic group and an aryl group as a substituent on the fatty chain in the case of an aliphatic group, it may have one or more substituents selected from the group consisting of a halogen atom, a nitro group, an alkyl group having from 1 to 6 carbon atoms and an alkoxyl group having from 1 to 6 carbon atoms), an alkyloxycarbonyl group having from 2 to 7 carbon atoms (the alkyl group moiety may have one or more substituents selected from the group consisting of a halogen atom and an alkoxyl groups having from 1 to 6 carbon atoms), or an aralkyloxycarbonyl group (wherein the aralkyl group has a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms)], which comprises the following steps 1, 2 and 3, Step 1:
a step in which an enantiomer mixture of a compound represented by formula (I):

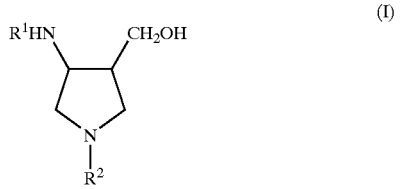

(in the formula, $R^1$ and $R^2$ are as defined in the foregoing, and the substituents $R^1HN$— and —$CH_2OH$ on the pyrrolidine ring are in the cis configuration) is treated with a compound represented by formula (II):

[in the formula,
$R^3$ and $R^4$ each independently represents
an alkyl group having from 1 to 6 carbon atoms (which may have one or more substituents selected from the group consisting of a halogen atom and an alkoxyl group having from 1 to 6 carbon atoms), or
an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms); or $R^3$ and $R^4$ may together form a cyclic structure of from five- to eight-membered ring comprised of a polymethylene chain] in the presence of an acid as an optically active compound, thereby obtaining a salt formed from a compound represented by a formula (IIIa):

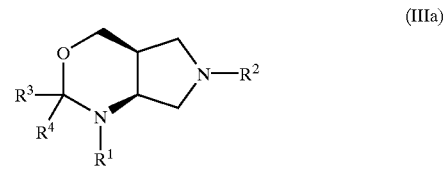

and the optically active acid,

Step 2:
a step in which a free form is obtained by removing the acid from the salt formed from the compound represented by formula (IIIa) and the optically active acid, and Step 3:
a step in which the compound represented by formula (Ia) is obtained by hydrolyzing the free form of the compound represented by formula (IIIa);

the aforementioned production method, wherein the acid as an optically active compound is D-mandelic acid;

the aforementioned production method, wherein $R^3$ and $R^4$ are the same group;

the aforementioned production method, wherein $R^3$ and $R^4$ are methyl group;

the aforementioned production method, wherein $R^1$ is a hydrogen atom;

the aforementioned production method, wherein $R^2$ is selected from the group consisting of a tert-butoxycarbonyl group, a 2,2,2-trichloroethoxycarbonyl group, a benzyloxycarbonyl group, a p-methoxybenzyloxycarbonyl group, a p-nitrobenzyloxycarbonyl group, an acetyl group, a methoxyacetyl group, a trifluoroacetyl group, a chloroacetyl group, a pivaloyl group, a formyl group and a benzoyl group; the aforementioned production method, wherein $R^2$ is a benzyloxycarbonyl group;

and so on.

MODE FOR CARRYING OUT THE INVENTION

The compound of the invention represented by formula (I) is described.

The substituent $R^1$ is a hydrogen atom, an alkyl group having from 1 to 6 carbon atoms, an aralkyl group, an acyl group, an alkyloxycarbonyl group having from 2 to 7 carbon atoms or an aralkyloxycarbonyl group. When $R^1$ is a group other than hydrogen atom, which has such a property that it can take a role as a protecting group and can be easily removed, such as benzyl group or the like, it is useful as a material compound that can be further converted into various compounds.

The alkyl group may be in the form of a straight chain or a branched chain or in a cyclic form. Also, this alkyl group may have one or more substituents selected from the group consisting of a halogen atom and an alkoxyl group having from 1 to 6 carbon atoms. Their substituting position is not particularly limited, but on the terminal carbon atom is desirable. As the halogen atom, fluorine atom or chlorine atom is desirable. The substitution number of halogen atoms may be one or more, but it may become a perfluoro substitution in the case of fluorine atom. The alkyl moiety of the alkoxyl group may also be in the form of a straight chain or a branched chain or in a cyclic form. As the alkyl group, a methyl group, an ethyl group, a propyl group, a butyl group, a trifluoromethyl group, a methoxymethyl group, a methoxyethyl group and the like are desirable.

The aralkyl group may have a structure in which an aryl group is substituted on an alkyl group having from 1 to 6 carbon atoms. The aryl group moiety thereof may have one or more substituents selected from the group consisting of a halogen atom, a nitro group, an alkyl group having from 1 to 6 carbon atoms and an alkoxyl group having from 1 to 6 carbon atoms. The alkyl group moiety may also have one or more substituents selected from the group consisting of alkyl groups having from 1 to 6 carbon atoms and alkoxyl groups having from 1 to 6 carbon atoms. These alkyl groups and alkyl moieties of the alkoxyl groups may be in the form of a straight chain or a branched chain or in a cyclic form. As the aralkyl group, a α-phenylethyl group, a benzyl group, a nitrobenzyl group, a trityl group, a toluyl group and the like are desirable.

The acyl group may be either aliphatic or aromatic. In the case of an aliphatic acyl group, it has from 2 to 7 carbon atoms and is either in straight chain or branched chain form. In addition, the fatty chain moiety may have one or more substituents selected from the group consisting of an aryl group, a halogen atom and an alkoxyl group having from 1 to 6 carbon atoms. Their substituting position is not particularly limited, but on the terminal carbon atom is desirable. As the halogen atom, chlorine atom or fluorine atom is desirable. The substitution number of halogen atoms may be one or more, and it may become a perfluoro substitution in the case of fluorine atom.

The aryl group as the substituent of aromatic acyl groups and of the fatty chain moiety of aliphatic acyl groups may have one or more substituents selected from the group consisting of a halogen atom, a nitro group, an alkyl group having from 1 to 6 carbon atoms and an alkoxyl group having from 1 to 6 carbon atoms. The alkyl moiety of these alkyl groups and alkoxyl groups may be in the form of a straight chain or a branched chain or in a cyclic form. As the acyl group, an acetyl group, a methoxyacetyl group, a trifluoroacetyl group, a chloroacetyl group, a pivaloyl group, a formyl group, a benzoyl group, a nitrophenylacetyl group and the like are desirable.

The alkyloxycarbonyl group may have from 2 to 7 carbon atoms. Its alkyl group moiety may have one or more substituents selected from the group consisting of a halogen atom and an alkoxyl group having from 1 to 6 carbon atoms. Fluorine atom or chlorine atom is desirable as the halogen atom, and the alkyl moiety of alkoxyl groups may be in the form of a straight chain or a branched chain or in a cyclic form. As the alkyloxycarbonyl group, a methoxycarbonyl group, a tert-butoxycarbonyl group, a 2,2,2-trichloroethoxycarbonyl group and the like are desirable.

Regarding the aralkyloxycarbonyl group, its aralkyl group moiety may be considered in the same manner as the aforementioned aralkyl group. As the aralkyloxycarbonyl group, a benzyloxycarbonyl group, a p-methoxybenzyloxycarbonyl group, a p-nitrobenzyloxycarbonyl group and the like are desirable.

The substituent $R^2$ is a hydrogen atom, an alkyl group having from 1 to 6 carbon atoms, an aralkyl group, an acyl group, an alkyloxycarbonyl group having from 2 to 7 carbon atoms or an aralkyloxycarbonyl group, and they can be considered in the same manner as the substituent $R^1$. Regarding the substituent $R^2$, preferred are a methyl group, an ethyl group, a propyl group, a butyl group, a trifluoromethyl group, a methoxymethyl group, a methoxyethyl group and the like as the alkyl group; a α-phenylethyl group, a benzyl group, a nitrobenzyl group, a trityl group, a toluyl group and the like as the aralkyl group; an acetyl group, a methoxyacetyl group, a trifluoroacetyl group, a chloroacetyl group, a pivaloyl group, a formyl group, a benzoyl group, nitrophenylacetyl group and the like as the acyl group; a methoxycarbonyl group, a tert-butoxycarbonyl group, a 2,2,2-trichloroethoxycarbonyl group and the like as the alkyloxycarbonyl group; and a benzyloxycarbonyl group, a p-methoxybenzyloxycarbonyl group, a p-nitrobenzyloxycarbonyl group and the like as the aralkyloxycarbonyl group.

The compound represented by formula (I) can be produced by the method shown as reference examples in this specification or, alternatively, can be produced by applying to this method certain modifications which can be generally considered by those skilled in the art.

Next, the compound represented by formula (II) is described.

(II)

In this case, the substituents $R^3$ and $R^4$ each independently represents an alkyl group having from 1 to 6 carbon atoms or an aralkyl group, or $R^3$ and $R^4$ may together form a cyclic structure of from five- to eight-membered ring comprised of a polymethylene chain.

These alkyl groups and aralkyl groups can be considered in the same manner as the substituent $R^1$. Regarding the substituents $R^3$ and $R^4$, preferred are a methyl group, an ethyl group, a propyl group, a butyl group, a trifluoromethyl group, a methoxymethyl group, a methoxyethyl group and the like as the alkyl group; a phenyl group, a dimethoxyphenyl group, a p-methoxyphenyl group and the like as the aryl group; and a α-phenylethyl group, a benzyl group, a nitrobenzyl group, a trityl group, a toluyl group and the like as the aralkyl group. Also, $R^3$ and $R^4$ may together form a cyclic structure of from five- to eight-membered ring (including the carbon atom to which $R^3$ and $R^4$ are bound) comprised of a polymethylene chain. When a cyclic structure is formed, size of the ring is preferably a five-membered ring or six-membered ring. This ring may be further substituted by a substituent, and an alkyl group is desirable as the substituent on the cyclic structure. When the cyclic structure has a substituent in this manner, it is desirable to introduce the substituent to effect enantiomorph. That is, it is desirable that the oxazine ring formed by the reaction of the compound of formula (II) with the compound of formula (I) does not generate new asymmetric center.

Since it is desirable that a new asymmetric center is not generated, $R^3$ and $R^4$ are preferably the same group. Acetone is particularly desirable as the ketone compound represented formula (II).

In the reaction for forming a condensed oxazine compound, it may be carried out using a solvent, and because of the presence of a ketone compound represented by formula (II), the examples of the solvent suited for this reaction include toluene, xylene and the like hydrocarbon solvents; diisopropyl ether, diethyl ether, tetrahydrofuran and the like ether solvents; chloroform, dichloromethane and the like halogenated hydrocarbon solvents; and ethyl acetate and the like esters. These may be used as a mixed solvent. On the other hand, a ketone compound represented by formula (II) can also be used by itself as a solvent. Practically, it is desirable to use a ketone compound represented by formula (II) serving also as a solvent. Also from such a point of view, acetone is desirable as the compound (II).

Regarding the amount of the solvent, a salt of the oxazine compound can be crystallized using approximately from 3 to 100 times, more preferably from about 6 to 20 times, particularly preferably about 10 times, of the solvent based on the compound represented by formula (I).

At the time of the reaction, mixing ratio of the compound represented by formula (I) and the acid as an optically active compound may be approximately from 0.1 to 3 moles, more preferably from about 0.5 to 2 moles, particularly preferably from about 1 to 1.25 moles, of the optically active acid based on 1 mole of the former compound. As a matter of course, the acid as an optically active compound is a pure substance (consisting of a single isomer) (the term "pure" as used herein means a chemically pure degree).

Crystallization of a salt of the condensed oxazine compound can be carried out at a temperature of from the melting point to boiling point of the solvent to be used, but is preferably from about −40 to 20° C., particularly preferably from −20 to 0° C.

The crystallization time may be 30 minutes or more, but preferably from about 20 to 80 hours, particularly preferably from about 40 to 60 hours.

Also, the thus precipitated salt of the condensed oxazine compound with optically active acid can be further purified by recrystallizing it or stirring it under a suspended condition in a solvent after collecting it by filtration. The solvent in this case is preferably acetone, but the aforementioned solvents can be optionally used. Also, the re-purification by recrystallization or stirring under a suspended condition in a solvent can be carried out between the melting point and boiling point of the solvent to be used, preferably at about −20 to 0° C.

The thus obtained salt of the condensed oxazine compound as an optically active compound represented by formula (III) with the acid as an optically active compound may sometimes contain the solvent used in the precipitation of salt and re-purification as a crystal solvent or adhered solvent. In addition, there will be a case in which it contains crystal water or adhered water.

The present invention also contemplates providing a method for obtaining a pure enantiomer compound represented by the formula (Ia) or (Ib), in which a salt of the cyclic compound as an optically active compound represented by formula (III) with the acid as an optically active compound is subjected to salt exchange by a base in an organic solvent and then to hydrolysis via the cyclic compound as a free optically active compound.

The base to be used in the salt exchange is an aqueous solution of hydroxide of sodium, potassium or the like alkali metal or triethylamine, pyridine or the like organic base, and an aqueous solution of hydroxide of sodium, potassium or the like alkali metal is preferable.

The solvent is toluene or the like hydrocarbon solvent, diisopropyl ether, diethyl ether or the like ether solvent, chloroform, dichloromethane or the like chlorine based solvent, ethyl acetate or a mixed solvent thereof, of which ethyl acetate is particularly desirable.

In this case, amount of the solvent is approximately from 3 to 50 times, preferably from about 5 to 20 times, particularly preferably from about 5 to 10 times, of the compound represented by formula (III).

Mixing ratio of the compound represented by formula (III) and the base is approximately from 1 to 3 moles, preferably from about 1 to 1.5 moles, particularly preferably from about 1 to 1.1 moles, of the base based on 1 mole of the compound represented by formula (III).

The reaction can be carried out at a temperature of from the melting point to boiling point of the solvent to be used, but is preferably from about 0 to 80° C., particularly preferably from 20 to 60° C.

The reaction time may be 30 minutes or more, but is preferably from about 1 to 12 hours, particularly preferably from about 3 to 6 hours.

In many cases, it is difficult to isolate the cyclic compound represented by formula (III), because the reaction partially proceeds to the optically active aminoalcohol derivative represented by the formula (I).

Hydrolysis of the cyclic compound represented by formula (III) can be carried out under either an acidic or basic condition.

In the case of an acidic condition, hydrochloric acid, sulfuric acid or the like inorganic acid or acetic acid, trifluoromethanesulfonic acid or the like organic acid may be used.

In the case of a basic condition, the base to be used is an aqueous solution of hydroxide of sodium, potassium or the like alkali metal or triethylamine, pyridine or the like organic base.

Among these conditions, preferred is an acidic condition, and hydrochloric acid aqueous solution is particularly desirable.

In the case of the acidic condition, the reaction can be carried out at a temperature of from the melting point to boiling point of the solvent to be used, but is preferably from about 0 to 30° C., particularly preferably from about 10 to 20° C.

In the case of the acidic condition, the reaction time may be 30 minutes or more, but is preferably from about 1 to 24 hours, particularly preferably from about 6 to 12 hours.

The method of the present invention can be applied to any compound in which amino group and hydroxyl group are substituted on such positions that a 1-oxa-3-aza cyclic compound of five-membered ring or six-membered ring can be formed by incorporating carbon atom of the ketone compound, so that its application is not limited to the compound of formula (I). The present inventors have considered that a or y-aminoalcohol compound is suitable as a compound to which the method of the invention can be applied. A compound represented by the following formula (A) can be cited as its illustrative example.

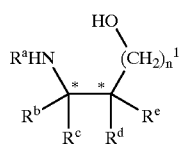

(A)

[In the formula, $R^a$ represents a hydrogen atom, an alkyl group having from 1 to 6 carbon atoms (which may have one or more substituents selected from the group consisting of a halogen atom and an alkoxyl group having from 1 to 6 carbon atoms), an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl groups having from 1 to 6 carbon atoms; and the alkyl group moiety may have one or more substituents selected from the group consisting of an alkyl group having from 1 to 6 carbon atoms and an alkoxyl group having from 1 to 6 carbon atoms), an acyl group (which may be either aliphatic or aromatic; in the case of an aliphatic group, it has from 1 to 7 carbon atoms and may have one or more substituents selected from the group consisting of an aryl group, a halogen atom and an alkoxyl group having from 1 to 6 carbon atoms; and in the cases of an aryl group as an aromatic group and an aryl group as a substituent on the fatty chain in the case of an aliphatic group, it may have one or more substituents selected from the group consisting of a halogen atom, a nitro group, an alkyl group having from 1 to 6 carbon atoms and an alkoxyl groups having from 1 to 6 carbon atoms), an alkyloxycarbonyl group having from 2 to 7 carbon atoms (the alkyl group moiety may have one or more substituents selected from the group consisting of a halogen atom and an alkoxyl group having from 1 to 6 carbon atoms), or an aralkyloxycarbonyl group (wherein the aralkyl group has a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms), $R^b$, $R^c$, $R^d$ and $R^e$ each independently represents a hydrogen atom, an alkyl group having from 1 to 6 carbon atoms (which may have one or more substituents selected from the group consisting of a halogen atom and an alkoxyl group having from 1 to 6 carbon atoms), or an aralkyl group (having a structure in which an aryl group is substituted on an alkyl group having from 1 to 6 carbon atoms; the aryl group moiety may have one or more substituents selected from the group consisting of a halogen atom, a nitro group, an alkyl groups having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms), with the proviso that $R^b$ and $R^c$ are not the same and/or $R^d$ and $R^e$ are not the same, and $n^1$ is 1 or 0.]

More preferred compound is a compound represented by the following formula (B) in which the substituents $R^c$ and $R^d$ in the aforementioned compound together form a cyclic structure. The present inventors have considered that this compound represented by the formula (B) gives a more rigid salt having good crystallinity when the salt is formed from a cyclic compound and an acid.

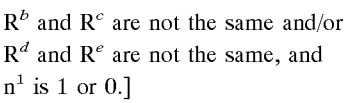

(B)

[In the formula, $R^a$, $R^b$, $R^e$ and $n^1$ are as defined in the foregoing, $Y^1$ represents a methylene group (>CH$_2$), a carbonyl group (>C=O) or a structure >CHR$^f$, $Y^2$ represents a methylene group (>CH$_2$), a carbonyl group (>C=O) or a structure >CHR$^g$, Z represents a methylene group (>CH$_2$), a carbonyl group (>C=O), a structure >CHR$^h$ or a structure >NR$^i$, $R^f$, $R^g$ and $R^h$ each independently represents an alkyl group having from 1 to 6 carbon atoms (which may have one or more substituents selected from the group consisting of a halogen atom and an alkoxyl group having from 1 to 6 carbon atoms), or an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl groups having from 1 to 6 carbon atoms), $R^i$ represents a hydrogen atom, an alkyl group having from 1 to 6 carbon atoms (which may have one or more substituents selected from the group consisting of a halogen atom and an alkoxyl group having from 1 to 6 carbon atoms), an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms), an acyl group (which may be either aliphatic or aromatic; in the case of an aliphatic group, it has from 1 to 7 carbon atoms and may have one or more substituents selected from the group consisting of an aryl group, a halogen atom and an alkoxyl groups having from 1 to 6 carbon atoms; and in the cases of an aryl group as an aromatic group and an aryl group as a substituent on the fatty chain in the case of an aliphatic group, it may have one or more substituents selected from the group consisting of a halogen atom, a nitro group, an alkyl group having from 1 to 6 carbon atoms and an alkoxyl group having from 1 to 6 carbon atoms), an alkyloxycarbonyl group having from 2 to 7 carbon atoms (the alkyl group moiety may have one or more substituents selected from the group consisting of a halogen atom and an alkoxyl groups having from 1 to 6 carbon atoms), or an aralkyloxycarbonyl group (wherein the aralkyl group has a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms), and each of $n^2$ and $n^3$ is independently an integer of 8 or less, with the proviso that the total of both cases is 3 or more and 8 or less ($3 \leq (n^2 + n^3) \leq 8$) (wherein the symbol ">" means bonding of an atom to its adjacent atom).]

Each of the substituents of compounds represented by formulae (A) and (B) can be considered in the same manner as the already described corresponding substituent.

Regarding the compound represented by formula (B), isomers are generated based on the amino group moiety and hydroxyl group moiety. That is, it exists in two cis and trans forms, and each of them exists in two isomer forms having enantiomorphic relationship. Though these isomers can be separated by the method of the invention, it is desirable to use a mixture of only cis form enantiomers or a mixture of only trans form enantiomers in carrying out the separation. These requirements can be applied in the same manner to the compound of formula (A).

An acidic condition is necessary in forming a 1-oxa-3-aza cyclic compound with the ketone compound, and the acid as an optically active compound to be used in the method of the invention takes a role in providing such an acidic condition. In addition, since this acid is optically active and the acid to be used in the practical reaction is comprised of only a single enantiomer, optical resolution is attained by forming a salt with one of the enantiomers of the compound of formula (A) or formula (B).

BEST MODE FOR CARRYING OUT THE INVENTION

Next, the present invention is described further illustratively based on Examples and Reference Examples, though the invention is not limited thereto.

EXAMPLE 1

1S,6S)-8-Benzyloxycarbonyl-4,4-dimethyl-5,8-diaza-3-oxabicyclo[4.3.0]nonane D-Mandelate

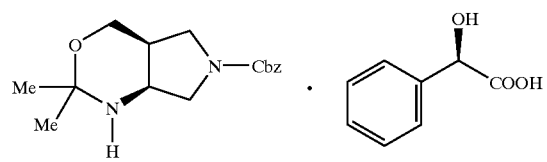

[Cbz: Benzyloxycarbonyl]

A mixture of 3,4-cis-3-amino-4-hydroxymethyl-N-benzyloxycarbonylpyrrolidine (racemic compound; 3.00 g) and D-mandelic acid (1.83 g) was dissolved in acetone (30 ml) at room temperature. After the dissolution, the resulting solution was stirred at −20° C. for 48 hours and then the thus precipitated salt was collected by filtration and dried at room temperature under a reduced pressure, thereby obtaining 2.26 g of the title compound.

Elemental analysis: $C_{24}H_{30}N_2O_6$; Calcd: C, 64.27; H, 6.89; N, 6.25; Found: C, 64.37; H, 6.76; N, 6.20; Melting point: 77–79° C.; MASS: m/e=291 (FABMS); $^1$H-NMR (DMSO-$d_6$) δ (ppm): 1.20 (3 H, s, 3-CHa), 1.30 (3 H, s, 3-CHb), (2.08 (s, acetone formed by decomposition of the title compound)), 3.15–4.00 (8 H, m, H1, H5a, H5b, H6, H7a, H7b), 4.90 (1 H, s, methine proton of D-mandelic acid), 5.06 (2 H, s, 8-$NCO_2CH_2$Ph), 7.25–7.42 (10 H, m, 8-$NCO_2CH_2$Ph, phenyl proton of D-mandelic acid).

(It was confirmed by NMR that the title compound was decomposed with passage of time in DMSO-$d_6$ to partially form 3-amino-4-hydroxymethyl-N-benzyloxycarbonylpyrrolidine and acetone. Assignment of the spectrum was described as the peak originated from the title compound.)

Optical purity: 95.6% ee (measured by inducing the salt into 3-(N-tert-butoxycarbonyl)amino-4-hydroxymethyl-N-benzyloxycarbonylpyrrolidine)

EXAMPLE 2

Spiro[(1S,6S)-5,8-diaza-8-benzyloxycarbonyl-3-oxabicyclo[4.3.0]nonane-4,1'-cyclohexane]D-Mandelate

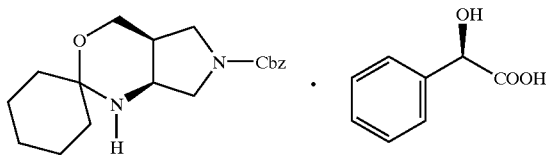

A mixture of 3,4-cis-3-amino-4-hydroxymethyl-N-benzyloxycarbonylpyrrolidine (racemic compound; 100 mg) and D-mandelic acid (61 mg) was dissolved in cyclohexanone (1 ml) at room temperature. After the dissolution, the resulting solution was stirred at 0° C. for 16 hours and then the thus precipitated salt was collected by filtration and washed with diisopropyl ether. This was dried at room temperature under a reduced pressure to obtain 57.8 mg of the title compound.

Elemental analysis: $C_{27}H_{34}N_2O_6$; Calcd: C, 67.20; H, 7.10; N, 5.80; Found: C, 67.27; H, 7.21; N, 5.59; Melting point: 144–147° C.; MASS: m/e=331 (FABMS); $^1$H-NMR (DMSO-$d_6$) δ (ppm): 1.30–1.97 (10 H, s, 3-cyclohexyl), 3.11–3.97 (8 H, overlapped the signals of H1, H5a, H5b, H6, H7a, H7b), 4.95 (1 H, s, methine proton of D-mandelic acid), 5.01 (2 H, s, 8-$NCO_2CH_2$Ph), 7.24–7.42 (10 H, m, 8-$NCO_2CH_2$Ph, phenyl proton of D-mandelic acid).

Optical purity: 97.5% ee (measured by inducing the salt into 3-(N-tert-butoxycarbonyl)amino-4-hydroxymethyl-N-benzyloxycarbonylpyrrolidine)

EXAMPLE 3

(1R,6R)-8-Benzyloxycarbonyl-4,4-dimethyl-5,8-diaza-3-oxabicyclo[4.3.0]nonane L-Mandelate

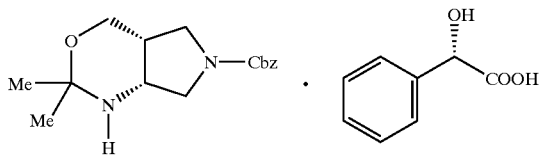

A mixture of 3,4-cis-3-amino-4-hydroxymethyl-N-benzyloxycarbonylpyrrolidine (racemic compound; 800 mg) and L-mandelic acid (488 mg) was dissolved in acetone (8 ml) at room temperature. After the dissolution, the resulting solution was stirred at −20° C. for 54 hours. The thus precipitated salt was collected by filtration and dried at room temperature under a reduced pressure to obtain 448 mg of the title compound.

Melting point: 86–87° C.

Optical purity: 95.8% ee (measured by inducing the salt to 3-(N-tert-butoxycarbonyl)amino-4-hydroxymethyl-N-benzyloxycarbonylpyrrolidine)

EXAMPLE 4

(3S,4S)-3-Amino-4-hydroxymethyl-N-benzyloxycarbonylpyrrolidine

A 670 g portion of (1S,6S)-2,8-diaza-3,3-dimethyl-4-oxa-8-benzyloxycarbonylbicyclo[4.3.0]nonane D-mandelate (optical purity: 97.8% ee) was mixed with 1 N hydrochloric acid aqueous solution (6,700 ml) and ethyl acetate (6,700 ml) and stirred to extract mandelic acid into the organic layer, the organic layer was removed and then the water layer was stirred at room temperature for 6 hours. After completion of the reaction, the aqueous solution was adjusted to strongly basic level with 5 N sodium hydroxide aqueous solution and extracted with chloroform (12,000 ml) three times (4,000 ml×3) and then the extracts were concentrated to dryness, thereby obtaining 373 g of the title compound.

Optical purity: 97.8% ee (measured by inducing the salt to 3-(N-tert-butoxycarbonyl)amino-4-hydroxymethyl-N-benzyloxycarbonylpyrrolidine)

REFERENCE EXAMPLE 1

1-Benzyloxycarbonyl-4-ethoxycarbonyl-3-oxopyrrolidine

Ethyl acrylate (65.01 ml, 600.0 mmol) was added to a toluene (1,200 ml) solution containing N-benzyloxycarbonylglycine ethyl ester (156.3 g, 600.0 mmol) and then, under ice-cooling, sodium hydride (60% oil; 26.40 g, 660.0 mmol) was added thereto. After 10 minutes of stirring at the same temperature, the ice bath was taken off, and the mixture was stirred at room temperature for 20 minutes and then at 50° C. for 3 hours. After completion of the reaction, and under ice-cooling, the reaction solution was adjusted to about pH 3 by adding 10% citric acid aqueous solution and mixed with ethyl acetate, and the mixture was shaken and then subjected to separation of layers. The organic layer was separated and washed with saturated brine, and the water layer was further extracted with ethyl acetate. The organic layers were dried over anhydrous sodium sulfate and then filtered, and the solvent was evaporated under a reduced pressure to obtain 196.7 g (600.0 mmol, quantitative) of the title compound.

$^1$H-NMR (400 MHz, CDCl$_3$) δ (ppm): 1.22–1.32 (3 H, m), 3.93–4.05 (1 H, m), 4.05–4.31 (5 H, m), 5.13–5.23 (2 H, m), 7.28–7.40 (5 H, m).

REFERENCE EXAMPLE 2

1-Benzyloxycarbonyl-4-ethoxycarbonyl-3-methoxyiminopyrrolidine

1-Benzyloxycarbonyl-4-ethoxycarbonyl-3-oxopyrrolidine (196.7 g, 600.0 mmol) was dissolved in pyridine (700 ml) and mixed with O-methylhydroxylamine hydrochloride (76.55 g, 916.5 mmol) under ice-cooling, and the mixture was stirred at the same temperature for 10 minutes and then at room temperature for 5 hours. Pyridine was evaporated under a reduced pressure, the residue was mixed with 1 N hydrochloric acid and ethyl acetate and then the mixture was shaken and subjected to separation of layers. The organic layer was washed with saturated brine, and the water layer was further extracted with ethyl acetate. The organic layers were dried over anhydrous sodium sulfate and filtered, the solvent was evaporated under a reduced pressure and then the residue was purified by a silica gel column chromatography (n-hexane:ethyl acetate=1:1) to obtain 187.5 g (589.1 mmol, 98.2%) of the title compound.

$^1$H-NMR (400 MHz, CDCl$_3$) δ (ppm): 1.15–1.32 (3 H, m), 3.55–4.05 (5 H, m), 4.05–4.25 (4 H, m), 5.09–5.20 (2 H, m), 7.28–7.40 (5 H, m).

REFERENCE EXAMPLE 3

3,4-cis-1-Benzyloxycarbonyl-3-tert-butoxycarbonylamino-4-hydroxymethylpyrrolidine 1-Benzyloxycarbonyl-4-ethoxycarbonyl-3-methoxyiminopyrrolidine (248.8 g, 550.0 mmol) was dissolved in anhydrous tetrahydrofuran (1,000 ml), a tetrahydrofuran solution of 1 M borane-tetrahydrofuran complex (2.75 l, 2.75 mol) was added dropwise to the above solution which was stirred at −78° C., and the mixture was stirred at the same temperature for 1.5 hours, under ice-cooling for 2 hours and then at room temperature for 12 hours. Under ice-cooling, water was added to the reaction solution until generation of gas stopped, and the solution was mixed with potassium carbonate (60.8 g) and stirred at room temperature for 1 hour. Next, the reaction solution was mixed with di-tert-butyl bicarbonate (144.0 g, 660.0 mmol) under ice-cooling and then stirred at room temperature for 16 hours. The reaction solution was mixed with water and ethyl acetate and shaken, and then the organic layer was separated. The organic layer was washed with saturated brine and then dried over anhydrous sodium sulfate. After filtration, the filtrate was concentrated under a reduced pressure. The thus obtained residue was crystallized. A portion of the thus precipitated crystals was purified by a silica gel column chromatography (n-hexane:ethyl acetate=2:1) and combined with the un-purified crystals to obtain 121.99 g (348.1 mmol, 63.3%) of the title compound.

$^1$H-NMR (400 MHz, CDCl$_3$) δ (ppm): 1.46 (9 H, s), 2.52–2.56 (1 H, m), 2.88–2.96 (1 H, m), 3.44–3.92 (6 H, m), 4.28 (1 H, br), 4.76–4.81 (1 H, m), 5.10 (1 H, d, J=13.0 Hz), 5.14 (1 H, d, J=13.0 Hz), 7.29–7.37 (5 H, m)

REFERENCE EXAMPLE 4

3,4-cis-3-Amino-4-hydroxymethyl-N-benzyloxycarbonylpyrrolidine 3-(N-tert-Butoxycarbonyl)amino-4-hydroxymethyl-N-benzyloxycarbonylpyrrolidine (10.0 g, 28.54 mmol) was dissolved in 1 N hydrochloric acid/ethanol (150 ml) and stirred at 45° C. for 15 hours. The reaction solution was evaporated under a reduced pressure, and the residue was mixed with dichloromethane and 1 N sodium hydroxide and shaken and then subjected to separation of layers. The organic layer was extracted and then the extract was concentrated to dryness to obtain 7.13 g (28.49 mmol, quantitative) of the title compound.

$^1$H-NMR (270 MHz, CDCl$_3$) δ (ppm): 2.29–2.41 (1 H, m, H4), 3.25–3.69 (5 H, m, H2a, H2b, H3, H5a, H5b), 3.80 (2 H, d, 4-CH$_2$OH), 5.13 (2 H, s, 1-NCO$_2$CH$_2$Ph), 7.30–7.37 (5 H, m, 1-NCO$_2$CH$_2$Ph) MASS: m/e=251 (FABMS).

What is claimed is:

1. A compound represented by the following formula (IIIa):

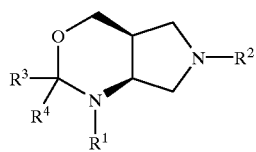

or formula (IIIb):

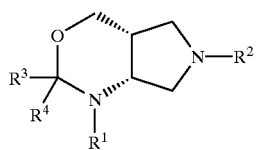

wherein $R^1$ represents a hydrogen atom, an alkyl group having from 1 to 6 carbon atoms (which may have one or more substituents selected from the group consisting of a halogen atom and an alkoxyl group having from 1 to 6 carbon atoms), an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl groups having from 1 to 6 carbon atoms), an acyl group (which may be either aliphatic or aromatic; in the case of an aliphatic group, it has from 1 to 7 carbon atoms and may have one or more substituents selected from the group consisting of an aryl group, a halogen atom and an alkoxyl group having from 1 to 6 carbon atoms, wherein said aryl group may have one or more substituents selected from the group consisting of a halogen atom, a nitro group, an alkyl group having from 1 to 6 carbon atoms and an alkyl group having from 1 to 6 carbon atoms; and in the case of an aromatic group, the aromatic moiety is an aryl group, wherein said aryl group may have one or more substituents selected from the group consisting of a halogen atom, a nitro group, an alkyl group having from 1 to 6 carbon atoms and an alkoxyl group having from 1 to 6 carbon atoms), an alkyloxycarbonyl group having from 2 to 7 carbon atoms (the alkyl group moiety may have one or more substituents selected from the group consisting of a halogen atom and an alkoxyl groups having from 1 to 6 carbon atoms), or an aralkyloxycarbonyl group (wherein the aralkyl group has a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms);

$R^2$ represents a hydrogen atom, an alkyl group having from 1 to 6 carbon atoms (which may have one or more substituents selected from the group consisting of a halogen atom and an alkoxyl group having from 1 to 6 carbon atoms), an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl groups having from 1 to 6 carbon atoms and an alkoxyl groups having from 1 to 6 carbon atoms), an acyl group (which may be either aliphatic or aromatic; in the case of an aliphatic group, it has from 1 to 7 carbon atoms and may have one or more substituents selected from the group consisting of an aryl group, a halogen atom and an alkoxyl group having from 1 to 6 carbon atoms; and in the cases of an aryl group as an aromatic group and an aryl group as a substituent on the fatty chain in the case of an aliphatic group, it may have one or more substituents selected from the group consisting of a halogen atom, a nitro group, an alkyl group having from 1 to 6 carbon atoms and an alkoxyl group having from 1 to 6 carbon atoms), an alkyloxycarbonyl group having from 2 to 7 carbon atoms (the alkyl group moiety may have one or more substituents selected from the group consisting of a halogen atom and an alkoxyl groups having from 1 to 6 carbon atoms), or an aralkyloxycarbonyl group (wherein the aralkyl group has a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms); and $R^3$ and $R^4$ each independently represents an alkyl group having from 1 to 6 carbon atoms (which may have one or more substituents selected from the group consisting of a halogen atom and an alkoxyl group having from 1 to 6 carbon atoms), or an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and alkoxyl group having from 1 to 6 carbon atoms; and the alkyl group moiety may have one or more substituents selected from the group consisting of an alkyl group having from 1 to 6 carbon atoms and a alkoxyl group having from 1 to 6 carbon atoms); or $R^3$ and $R^4$ may together form a cyclic structure of from five- to eight-membered ring consisting of a polymethylene chain.

2. A salt and a hydrate thereof, formed from a compound represented by the formula (IIIa) or formula (IIIb) according to claim 1 and an acid as an optically active compound.

3. The salt and a hydrate thereof according to claim 2, wherein the acid as an optically active compound is D-mandelic acid or L-mandelic acid.

4. The salt and a hydrate thereof according to claim 2, wherein the acid as an optically active compound is D-mandelic acid.

5. The salt and a hydrate thereof according to claim 2, wherein the acid as an optically active compound is L-mandelic acid.

6. The salt and a hydrate thereof according to any one of claims 2 to 5, wherein $R^3$ and $R^4$ are the same group.

7. The salt and a hydrate thereof according to any one of claims 2 to 5, wherein $R^3$ and $R^4$ are a methyl group.

8. The salt and a hydrate thereof according to any one of claims 2 to 7, wherein $R^1$ is a hydrogen atom.

9. The salt and a hydrate thereof according to any one of claims 2 to 8, wherein $R^2$ is selected from the group consisting of a tert-butoxycarbonyl group, a 2,2,2-trichloroethoxycarbonyl group, a benzyloxycarbonyl group, a p-methoxybenzyloxycarbonyl group, a p-nitrobenzyloxycarbonyl group, an acetyl group, a methoxyacetyl group, a trifluoroacetyl group, a chloroacetyl group, a pivaloyl group, a formyl group and a benzoyl group.

10. The salt and a hydrate thereof according to any one of claims 2 to 8, wherein $R^2$ is a benzyloxycarbonyl group.

11. A method for producing a compound represented by a formula (Ia):

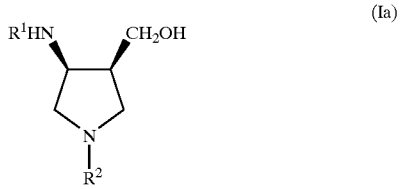

(Ia)

or formula (Ib):

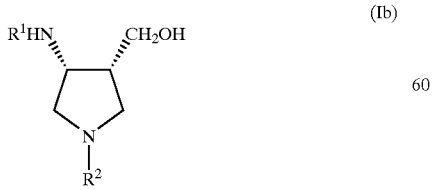

(Ib)

wherein
$R^1$ represents a hydrogen atom, an alkyl group having from 1 to 6 carbon atoms (which may have one or more substituents selected from the group consisting of a halogen atom and an alkoxyl group having from 1 to 6 carbon atoms), an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl groups having from 1 to 6 carbon atoms),an acyl group (which may be either aliphatic or aromatic; in the case of an aliphatic group, it has from 1 to 7 carbon atoms and may have one or more substituents selected from the group consisting of an aryl group, a halogen atom and an alkoxyl group having from 1 to 6 carbon atoms, wherein said aryl group may have one or more substituents selected from the group consisting of a halogen atom, a nitro group, an alkyl group having from 1 to 6 carbon atoms and an alkoxyl group having from 1 to 6 carbon atoms; and in the case of an aromatic group, the aromatic moiety is an aryl group, wherein said aryl group may have one or more substituents selected from the group consisting of a halogen atom, a nitro group, an alkyl group having from 1 to 6 carbon atoms and an alkoxyl group having from 1 to 6 carbon atoms), an alkyloxycarbonyl group having from 2 to 7 carbon atoms (the alkyl group moiety may have one or more substituents selected from the group consisting of a halogen atom and an alkoxyl groups having from 1 to 6 carbon atoms), or an aralkyloxycarbonyl group (wherein the aralkyl group has a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms); and $R^2$ represents a hydrogen atom, an alkyl group having from 1 to 6 carbon atoms (which may have one or more substituents selected from the group consisting of a halogen atom and an alkoxyl group having from 1 to 6 carbon atoms), an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl groups having from 1 to 6 carbon atoms and an alkoxyl groups having from 1 to 6 carbon atoms), an acyl group (which may be either aliphatic or aromatic; in the case of an aliphatic group, it has from 1 to 7 carbon atoms and may have one or more substituents selected from the group consisting of an aryl group, a halogen atom and an alkoxyl group having from 1 to 6 carbon atoms; and in the cases of an aryl group as an aromatic group and an aryl group as a substituent on the fatty chain in the case of an aliphatic group, it may have one or more substituents selected from the group consisting of a halogen atom, a nitro group, an alkyl group having from 1 to 6 carbon atoms and an alkoxyl group having from 1 to 6 carbon atoms), an alkyloxycarbonyl group having from 2 to 7 carbon atoms (the alkyl group moiety may have one or more substituents selected from the group consisting of a halogen atom and an alkoxyl group having from 1 to 6 carbon atoms), or an aralkyloxycarbonyl group (wherein the aralkyl group has a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms), which comprises the following steps 1, 2 and 3, Step 1:

a step which an enantiomer mixture of a compound represented by a formula (I):

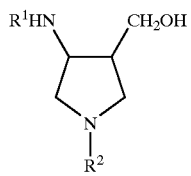

(I)

wherein $R^1$ and $R^2$ are as defined in the foregoing, and the substituents $R^1HN$— and —$CH_2OH$ on the pyrrolidine ring are in the cis configuration, is treated with a compound represented by formula (II):

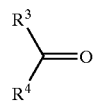

(II)

wherein $R^3$ and $R^4$ each independently represents an alkyl group having from 1 to 6 carbon atoms (which may have one or more substituents selected from the group consisting of a halogen atom and an alkoxyl group having from 1 to 6 carbon atoms), or an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms); or $R^3$ and $R^4$ may together form a cyclic structure of from five- to eight-membered ring comprised of a polymethylene chain in the presence of an acid as an optically active compound, thereby obtaining a salt formed from either of a compound represented by formula (IIIa):

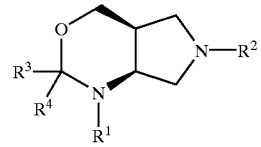

(IIIa)

or a formula (IIIb):

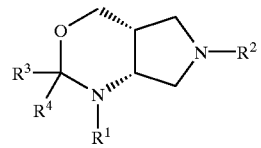

(IIIb)

and the optically active acid,

Step 2:

a step in which a free form is obtained by removing the acid from the salt formed from the compound represented by formula (IIIa) or (IIIb) and the optically active acid, and Step 3:

a step in which the compound represented by formula (Ia) or (Ib) is obtained by hydrolyzing free form of the compound represented by the formula (IIIa) or (IIIb).

12. The production method according to claim 11, wherein the acid as an optically active compound is D-mandelic acid or L-mandelic acid.

13. A method for producing a compound represented by a formula (Ia):

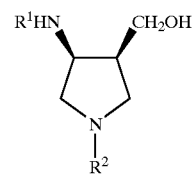

(Ia)

wherein $R^1$ represents a hydrogen atom, an alkyl group having from 1 to 6 carbon atoms (which may have one or more substituents selected from the group consisting of a halogen atom and an alkoxyl group having from 1 to 6 carbon atoms), an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl groups having from 1 to 6 carbon atoms), an acyl group (which may be either aliphatic or aromatic; in the case of an aliphatic group, it has from 1 to 7 carbon atoms and may have one or more substituents selected from the group consisting of an aryl group, a halogen atom and an alkoxyl group having from 1 to 6 carbon atoms, wherein said aryl group may have one or more substituents selected from the group consisting of a halogen atom, a nitro group, an alkyl group having from 1 to 6 carbon atoms and an alkoxyl group having from 1 to 6 carbon atoms; and in the case of an aromatic group, the aromatic moiety is an aryl group, wherein said aryl group may have one or more substituents selected from the group consisting of a halogen atom, a nitro group, an alkyl group having from 1 to 6 carbon atoms and an alkoxyl group having from 1 to 6 carbon atoms), an alkyloxycarbonyl group having from 2 to 7 carbon atoms (the alkyl group moiety may have one or more substituents selected from the group consisting of a halogen atom and an alkoxyl groups having from 1 to 6 carbon atoms), or an aralkyloxycarbonyl group (wherein the aralkyl group has a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms); and $R^2$ represents a hydrogen atom, an alkyl group having from 1 to 6 carbon atoms (which may have one or more substituents selected from the group consisting of a halogen atom and an alkoxyl group having from 1 to 6 carbon atoms), an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl groups having from 1 to 6 carbon atoms and an alkoxyl groups having from 1 to 6 carbon atoms), an acyl group (which may be either aliphatic or aromatic; in the case of an aliphatic group, it has from 1 to 7 carbon atoms and may have one or more substituents selected from the group consisting of an aryl group, a halogen atom and an alkoxyl group having from 1 to 6 carbon atoms; and in the cases of an aryl group as an aromatic group and an aryl group as a substituent on the fatty chain in the case of an aliphatic group, it may have one or more substituents selected from the group consisting of a halogen atom, a nitro group, an alkyl group having from 1 to 6 carbon atoms and an alkoxyl group having from 1 to 6 carbon atoms), an alkyloxycarbonyl group having from 2 to 7 carbon atoms (the alkyl group moiety may have one or more substituents selected from the group consisting of a halogen atom and an alkoxyl groups having from 1 to 6 carbon atoms), or an aralkyloxycarbonyl group (wherein the aralkyl group has a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms), which comprises the following steps 1, 2 and 3, Step 1:

a step in which an enantiomer mixture of a compound represented by a formula (I):

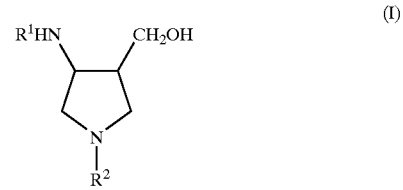

wherein $R^1$ and $R^2$ are as defined in the foregoing, and the substituents $R^1HN$— and —$CH_2HO$ on the pyrrolidine ring are in the cis configuration, is treated with a compound represented by formula (II):

wherein $R^3$ and $R^4$ each independently represents an alkyl group having from 1 to 6 carbon atoms (which may have one or more substituents selected from the group consisting of a halogen atom and an alkoxyl group having from 1 to 6 carbon atoms), or an aralkyl group (having a structure in which an aryl group is substituted on an alkyl group having from 1 to 6 carbon atoms; the aryl group moiety may have one or more substituents selected from the group consisting of a halogen atom, a nitro group, an alkyl group having from 1 to 6 carbon atoms and an alkoxyl group having from 1 to 6 carbon atoms; and the alkyl group moiety may have one or more substituents selected from the group consisting of an alkyl group having from 1 to 6 carbon atoms and an alkoxyl group having from 1 to 6 carbon atoms); or $R^3$ and $R^4$ may together form a cyclic structure of from five- to eight-membered ring comprised of a polymethylene chain, in the presence of an acid as an optically active compound, thereby obtaining a salt formed from a compound represented by a formula (IIIa):

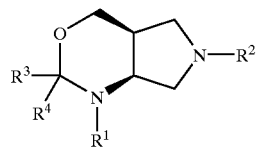

(IIIa)

and the optically active acid,

Step 2:
a step in which a free compound is obtained by removing the acid from the salt formed from the compound represented by formula (IIa) and the optically active acid, and Step 3:
a step in which the compound represented by formula (Ia) is obtained by hydrolyzing free form of the compound represented by the formula (IIIa).

14. The production method according to claim 13, wherein the acid as an optically active compound is D-mandelic acid.

15. The production method according to any one of claims 11 to 14, wherein $R^3$ and $R^4$ are the same group.

16. The production method according to any one of claims 11 to 14, wherein $R^3$ and $R^4$ are a methyl group.

17. The production method according to any one of claims 11 to 14, wherein $R^1$ is a hydrogen atom.

18. The production method according to any one of claims 11 to 14, wherein $R^2$ is selected from the group consisting of a tert-butoxycarbonyl group, a 2,2,2-trichloroethoxycarbonyl group, a benzyloxycarbonyl group, a p-methoxybenzyloxycarbonyl group, a p-nitrobenzyloxycarbonyl group, an acetyl group, a methoxyacetyl group, a trifluoroacetyl group, a chloroacetyl group, a pivaloyl group, a formyl group and a benzoyl group.

19. The production method according to any one of claims 11 to 14, wherein $R^2$ is a benzyloxycarbonyl group.

* * * * *